(12) United States Patent
Vo et al.

(10) Patent No.: US 6,720,308 B1
(45) Date of Patent: Apr. 13, 2004

(54) ANHYDROLIDE DERIVATIVES HAVING ANTIBACTERIAL ACTIVITY

(75) Inventors: Nha Huu Vo, Malden, MA (US); Ying Hou, Everett, MA (US); Ly Tam Phan, Malden, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 10/289,820

(22) Filed: Nov. 7, 2002

(51) Int. Cl.[7] ............... A01N 43/04; A61K 31/70; C07H 17/08
(52) U.S. Cl. ............... 514/29; 536/7.2; 536/7.3; 536/7.4
(58) Field of Search ............... 514/29; 536/7.2, 536/7.3, 7.4

(56) References Cited

U.S. PATENT DOCUMENTS 6,124,269 A    9/2000  Phan et al. ............... 514/29

FOREIGN PATENT DOCUMENTS

| WO | WO 97/42205 | * 11/1997 | |
| WO | WO 97/42205 A1 | 11/1997 | ............ C07H/17/08 |
| WO | WO 02/16380 A1 | * 2/2002 | |
| WO | WO 02/50091 A1 | 6/2002 | ............ C07H/17/08 |
| WO | WO 02/50092 A1 | 6/2002 | ............ C07H/17/08 |
| WO | WO 03/024986 | 3/2003 | ............ C07H/17/08 |

OTHER PUBLICATIONS

Anhydrolide Macrolides. 1. Sythesis and Antibacterial Activity of 2,3–Anhydro–6–O–methyl 11,12–Carbamate Erythromycin A Analogs, Elliott et al, J. Med. Chem. 1998, 41, 1651–1659.

Anhydrolide Macrolides. 2. Sythesis and Antibacterial Activity of 2,3–Anhydro–6–O–methyl 11,12–Carbazate Erythromycin A Analogs, Griesgraber et al., J. Med. Chem. 1998, 41, 1660–1670.

* cited by examiner

Primary Examiner—James O. Wilson
Assistant Examiner—Traviss C. McIntosh, III
(74) Attorney, Agent, or Firm—Jason D. Ferrone; Gaetano D. Maccarone

(57) ABSTRACT

Novel 11-12 substituted lactone anhydrolide derivatives and pharmaceutically-acceptable compositions comprising a therapeutically effective amount of a compound of the invention in combination with a pharmaceutically-acceptable carrier are described. Also described are a method for treating bacterial infections by administering to an animal a pharmaceutical composition containing a therapeutically effective amount of a compound of the invention and processes for the preparation of such compounds.

6 Claims, No Drawings

ANHYDROLIDE DERIVATIVES HAVING ANTIBACTERIAL ACTIVITY

REFERENCE TO RELATED APLICATIONS

Reference is made to prior copending, commonly assigned application Ser. No. 10/223,144, filed Aug. 19, 2002.

TECHNICAL FIELD

The present invention relates to novel macrolides having antibacterial activity and useful in the treatment and prevention of bacterial infections. More particularly, the invention relates to novel 11,12-lactone anhydrolides, a 14-membered macrolides, compositions containing such compounds and methods for using the same, as well as processes for making such compounds.

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Macrolides are classified according to the size of the lactone ring (12, 14, 15 or 16 atoms). The macrolide antibiotic families (14-, 15- and 16-membered ring derivatives) exhibit a wide range of characteristics (antibacterial spectrum, side-effects and bioavailability). Among the commonly used macrolides are erythromycin, clarithromycin and azithromycin.

Erythromycins A through D, represented by formula (E) as illustrated below,

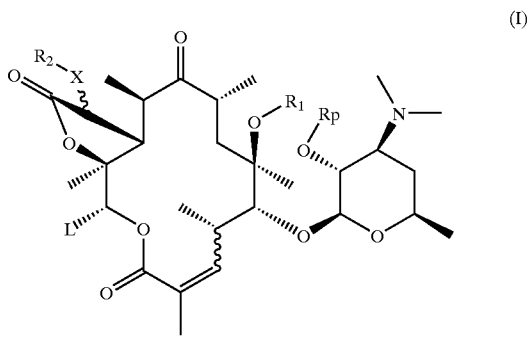

| Erythromycin | $R^a$ | $R^b$ |
|---|---|---|
| A | —OH | —CH3 |
| B | —H | —CH3 |
| C | —OH | —H |
| D | —H | —H | are well-known and potent antibacterial agents and are used widely to treat and prevent bacterial infection. As with other antibacterials, however, bacterial strains having resistance or insufficient susceptibility to erythromycin have been identified. Also, erythromycin A has only weak activity against Gram-negative bacteria. Therefore, there is a continuing need to identify new erythromycin derivative compounds which possess improved antibacterial activity, which have less potential for developing resistance, which possess the desired Gram-negative activity, or which possess unexpected selectivity against target microorganisms. Consequently, numerous investigators have prepared chemical derivatives of erythromycin in an attempt to obtain analogs having modified or improved profiles of antibiotic activity.

International Application WO 97/42205 of Elliott et al, published Nov. 13, 1997, discloses 3-descladinose-2,3-anhydroerythromycin derivatives having a cyclic carbamate and cyclic carbazate basic nuclear structure. Further details were also disclosed in *J. Med Chem.*, 41, pp 1651–1659 (1998) and *J. Med Chem.*, 41, pp 1660–1670 (1998) by Elliott et al, and by Griesgraber et al, respectively.

Erythromycin derivatives containing an 11,12-γ-lactone moiety are disclosed in International Applications WO 02/16380, WO 02/50091, and WO 02/50092.

SUMMARY OF THE INVENTION

The present invention provides a novel class of 14-membered macrolide compounds possessing antibacterial activity toward Gram positive and Gram negative bacteria as well as macrolide resistant Gram positives. The compounds of the present invention are represented by the general formula (I) as illustrated below

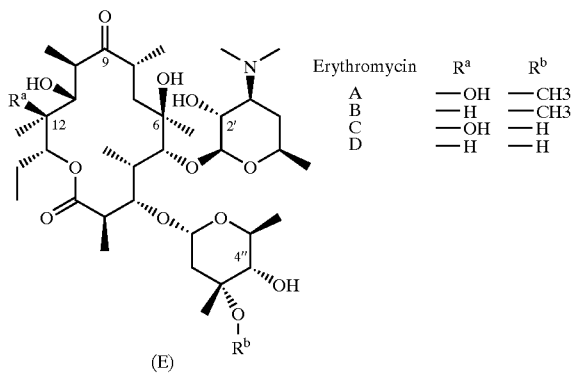

(I)

as well as the pharmaceutically acceptable salts, esters or prodrugs thereof. In formula (I) above:

L is selected from the group consisting of:
(1) —CH(OH)CH$_3$;
(2) C$_1$–C$_6$ alkyl, optionally substituted with one or more substituents selected from the group consisting of aryl, substituted aryl, heteroaryl and substituted heteroaryl;
(3) C$_2$–C$_6$ alkenyl, optionally substituted with one or more substituents selected from the group consisting of aryl, substituted aryl, heteroaryl and substituted heteroaryl; and
(4) C$_2$–C$_6$ alkynyl, optionally substituted with one or more substituents selected from the group consisting of aryl, substituted aryl, heteroaryl and substituted heteroaryl;

R$_1$ is selected from the group consisting of C$_1$–C$_6$-alkyl, C$_2$–C$_6$-alkenyl and C$_2$–C$_6$-alkynyl, each optionally substituted with one or more substituents selected from the group consisting of:
(1) halogen;
(2) aryl;
(3) substituted aryl;
(4) heteroaryl;
(5) substituted heteroaryl;
(6) —O—R$_5$, where R$_5$ is selected from the group consisting of:
  a. hydrogen;
  b. aryl;
  c. substituted aryl;
  d. heteroaryl; and
  e. substituted heteroaryl;
(7) —O—C$_1$–C$_6$-alkyl-R$_5$, where R$_5$ is as previously defined;
(8) —O—C$_2$–C$_6$-alkenyl-R$_5$; where R$_5$ is as previously defined;
(9) —O—C$_2$–C$_6$-alkynyl-R$_5$, where R$_5$ is as previously defined; and

(10) —$NR_6R_7$, where $R_6$ and $R_7$ are each independently selected from the group consisting of: hydrogen; $C_1$–$C_6$-alkyl, optionally substituted with one or more substituents selected from the group consisting of halogen, aryl, substituted aryl, heterocyclic and substituted heterocyclic; $C_2$–$C_6$-alkenyl, optionally substituted with one or more substituents selected from the group consisting of halogen, aryl, substituted aryl, heterocyclic and substituted heterocyclic; and $C_2$–$C_6$-alkynyl, optionally substituted with one or more substituents selected from the group consisting of halogen, aryl, substituted aryl, heterocyclic and substituted heterocyclic; or $R_6R_7$ taken together with the nitrogen atom to which they are attached form a 3- to 7-membered ring which may optionally contain one or more hetero functions selected from the group consisting of —O—, —NH—, —N($C_1$–$C_6$-alkyl)-, —N(aryl)-, —N(heteroaryl)-, —S—, —S(O)— and —S(O)$_2$—;

$R_2$ is selected from the group consisting of:
(1) hydrogen;
(2) $C_1$–$C_6$-alkyl, optionally substituted with one or more substituents selected from the group consisting of:
  a. halogen;
  b. aryl;
  c. substituted aryl;
  d. heterocyclic;
  e. substituted heterocyclic;
  f. —O—$R_3$, where $R_3$ is selected from the group consisting of:
    i. hydrogen;
    ii. aryl;
    iii. substituted aryl;
    iv. heteroaryl; and
    v. substituted heteroaryl;
  g. —O—$C_1$–$C_6$-alkyl-$R_3$, where $R_3$ is as previously defined;
  h. —O—$C_2$–$C_6$-alkenyl-$R_3$, where $R_3$ is as previously defined;
  i. —O—$C_2$–$C_6$-alkynyl-$R_3$, where $R_3$ is as previously defined; and
  j. —$NR_6R_7$, where $R_6$ and $R_7$ are as previously defined;
(3) $C_2$–$C_6$-alkenyl, optionally substituted with one or more substituents selected from the group consisting of:
  a. halogen;
  b. aryl;
  c. substituted aryl;
  d. heterocyclic;
  e. substituted heterocyclic;
  f. —O—$R_3$, where $R_3$ is as previously defined;
  g. —O—$C_1$–$C_6$-alkyl-$R_3$, where $R_3$ is as previously defined;
  h. —O—$C_2$–$C_6$-alkenyl-$R_3$, where $R_3$ is as previously defined;
  i. —O—$C_2$–$C_6$-alkynyl-$R_3$, where $R_3$ is as previously defined; and
  j. —$NR_6R_7$, where $R_6$ and $R_7$ are as previously defined; and
(4) $C_2$–$C_6$-alkynyl, optionally substituted with one or more substituents selected from the group consisting of:
  a. halogen;
  b. aryl;
  c. substituted aryl;
  d. heterocyclic;
  e. substituted heterocyclic;
  f. —O—$R_3$, where $R_3$ is as previously defined;
  g. —O—$C_1$–$C_6$-alkyl-$R_3$, where $R_3$ is as previously defined;
  h. —O—$C_2$–$C_6$-alkenyl-$R_3$, where $R_3$ is as previously defined;
  i. —O—$C_2$–$C_6$-alkynyl-$R_3$, where $R_3$ is as previously defined; and
  j. —$NR_6R_7$, where $R_6$ and $R_7$ are as previously defined;

X is selected from the group consisting of:
(a) S(O)n, where n is 0, 1, or 2;
(b) O; and
(c) $NR_5$, where $R_5$ is as previously defined; and Rp is hydrogen or a hydroxy protecting group.

In another aspect of the present invention there are disclosed pharmaceutical compositions comprising a therapeutically effective amount of a compound of the invention in combination with a pharmaceutically acceptable carrier and treatment of bacterial infections with such compositions. Suitable carriers and methods of formulation are also disclosed. The compounds and compositions of the present invention have antibacterial activity.

In a further aspect of the present invention there are provided processes for the preparation of bicyclic macrolide derivatives of formula (I) wherein L, X, $R_1$, $R_2$ and Rp are as previously described.

DETAILED DESCRIPTION OF THE INVENTION

A first embodiment of the present invention includes compounds represented by formula (I), as illustrated above, as well as the pharmaceutically acceptable salts, esters and prodrugs thereof.

A preferred group of compounds of the present invention are those represented by formula (I) wherein L is ethyl, X is sulfur, $R_1$ is methyl, and where $R_2$ and Rp are as previously defined.

Representative compounds of the invention are those selected from the group consisting of:

Compound of formula (I): L=$CH_2CH_3$, X=S, $R_1$=$CH_3$, $R_2$=2-[6-(dimethylamino-methyleneamino)purin-9-yl]-ethyl and Rp=H;

Compound of formula (I): L=$CH_2CH_3$, X=S, $R_1$=$CH_3$, $R_2$=2-(6-amino-purin-yl)-ethyl and Rp=H;

Compound of formula (I): L=$CH_2CH_3$, X=S, $R_1$=$CH_3$, $R_2$=3-(3-pyridinyl)-1H-pyrazole-ethyl and Rp=H;

Compound of formula (I): L=$CH_2CH_3$, X=S, $R_1$=$CH_3$, $R_2$=[3-(3-pyridinyl)-1H-1,2,4-triazole-1-yl]-ethyl and Rp=H;

Compound of formula (I): L=$CH_2CH_3$, X=S, $R_1$=$CH_3$, $R_2$=[4-(3-pyridinyl)-1H-imidazole]-1-ethyl and Rp=H; and Compound of formula (I): L=$CH_2CH_3$, X=O, $R_1$=$CH_3$, $R_2$=$CH_2CH_2$-phenyl and Rp=H.

Definitions

The terms "$C_1$–$C_3$ alkyl," "$C_1$–$C_6$ alkyl" or "$C_1$–$C_{12}$ alkyl," as used herein, refer to saturated, straight- or branched-chain hydrocarbon radicals containing between one and three, one and six, or one and twelve carbon atoms, respectively. Examples of $C_1$–$C_3$ alkyl radicals include methyl, ethyl, propyl and isopropyl radicals; examples of $C_1$–$C_6$ alkyl radicals include, but are not limited to, methyl, ethyl, propyl, isopropyl, n-butyl, tert-butyl, neopentyl and n-hexyl radicals; and examples of $C_1$–$C_{12}$ alkyl radicals include, but are not limited to, methyl, ethyl, n-propyl, isopropyl, n-hexyl, n-octyl, n-decyl and n-dodecyl radicals.

The terms "$C_2$–$C_6$ alkenyl" or "$C_2$–$C_{12}$ alkenyl," as used herein, denote a monovalent group derived from a hydrocarbon moiety containing from two to six or two to twelve carbon atoms having at least one carbon-carbon double bond by the removal of a single hydrogen atom. Alkenyl groups include, but are not limited to, ethenyl, propenyl, isobutenyl, 1,3-hexadienyl, n-hexenyl, 3-pentenyl, 1-methyl-2-buten-1-yl, and the like.

The terms "$C_2$–$C_6$ alkynyl" or "$C_2$–$C_{12}$ alkynyl," as used herein, denote a monovalent group derived from a hydrocarbon moiety containing from two to six or two to twelve carbon atoms having at least one carbon-carbon triple bond by the removal of two hydrogen atoms. Representative alkynyl groups include, but are not limited to, ethynyl, 1-propynyl, 1-butynyl, isopentynyl, 1,3-hexadiynyl, n-hexynyl, 3-pentynyl, 1-hexen-3-ynyl and the like.

The terms "halo" and "halogen," as used herein, refer to an atom selected from fluorine, chlorine, bromine and iodine.

The term "haloalkyl" denotes an alkyl group, as defined above, having one, two or three halogen atoms attached thereto and is exemplified by such groups as chloromethyl, bromoethyl, trifluoromethyl, and the like.

The term "aryl," as used herein, refers to a mono-, bicyclic or tricyclic carbocyclic ring system having one, two or three aromatic rings including, but not limited to, phenyl, naphthyl, anthryl, azulyl, tetrahydronaphthyl, indanyl, indenyl and the like.

The term "substituted aryl," as used herein, refers to an aryl group, as defined herein, substituted by independent replacement of one or more of the hydrogen atoms thereon with substituents independently selected from substituents such as, but not limited to, alkyl, haloalkyl, alkoxy, thioalkoxy, amino, alkylamino, dialkylamino, acylamino, hydroxy, cyano, halo, mercapto, nitro, carboxaldehyde, carboxyl, alkoxycarbonyl, carboxamide, aryl, substituted aryl, heteroaryl, substituted heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, thio, aryl-thio, heteroarylthio, benzyl-thio, $C_1$–$C_6$-alkyl-thio, or methylthiomethyl. Representative substituents include, but are not limited to, F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, tetrafluorophenyl and pentafluorophenyl.

The term "heteroaryl," as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "substituted heteroaryl," as used herein, refers to a heteroaryl group as defined herein, substituted by independent replacement of one, or more of the hydrogen atoms thereon with substituents independently selected from substituents such as, but not limited to, alkyl, haloalkyl, alkoxy, thioalkoxy, amino, alkylamino, dialkylamino, acylamino, hydroxy, cyano, halo, mercapto, nitro, carboxaldehyde, carboxyl, alkoxycarbonyl, carboxamide, aryl, substituted aryl, heteroaryl, substituted heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, thio, aryl-thio, heteroarylthio, benzyl-thio, $C_1$–$C_6$-alkyl-thio, or methylthiomethyl. Representative substituents include, but are not limited to, F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, tetrafluorophenyl and pentafluorophenyl.

The term "$C_3$–$C_{12}$-cycloalkyl", as used herein, denotes a monovalent group derived from a monocyclic or bicyclic saturated carbocyclic ring compound having from 3 to 12 carbon atoms by the removal of a single hydrogen atom. Examples include, but not limited to, cyclopropyl, cyclobutyl, cyclopentyl, cyclohexyl, bicyclo [2.2.1] heptyl, and bicyclo [2.2.2] octyl.

The term "substituted $C_3$–$C_{12}$-cycloalkyl", as used herein, refers to a $C_3$–$C_{12}$-cycloalkyl group, as defined herein, substituted by independent replacement of one or more of the hydrogen atoms therein with substituents independently selected from substituents such as, but not limited to, alkyl, haloalkyl, alkoxy, thioalkoxy, amino, alkylamino, dialkylamino, acylamino, hydroxy, cyano, halo, mercapto, nitro, carboxaldehyde, carboxyl, alkoxycarbonyl, carboxamide, aryl, substituted aryl, heteroaryl, substituted heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, thio, aryl-thio, heteroarylthio, benzyl-thio, $C_1$–$C_6$-alkyl-thio, or methylthiomethyl. Representative substituents include, but are not limited to, F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, tetrafluorophenyl and pentafluorophenyl.

The term "$C_1$–$C_3$-alkyl-$C_3$–$C_5$-cycloalkyl", as used herein, refers to a $C_3$–$C_5$ cycloalkyl radical, as defined herein, attached to a $C_1$–$C_3$-alkyl radical by replacement of a hydrogen atom on the latter.

The term "heterocycloalkyl," as used herein, refers to a non-aromatic 3-, 4-, 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "substituted heterocycloalkyl", as used herein, refers to a cycloalkyl group, as gefined herein, substituted by independent replacement of one or more of the hydrogen atoms therein with substituents independently selected from substituents such as, but not limited to, alkyl, haloalkyl, alkoxy, thioalkoxy, amino, alkylamino, dialkylamino, acylamino, hydroxy, cyano, halo, mercapto, nitro, carboxaldehyde, carboxyl, alkoxycarbonyl, carboxamide, aryl, substituted aryl, heteroaryl, substituted heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, thio, arylthio, heteroarylthio, benzyl-thio, $C_1$–$C_6$-alkyl-thio, or methylthiomethyl. Representative substituents include, but are not limited to, F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, tetrafluorophenyl and pentafluorophenyl.

The term "heterocyclic", as used herein, refers to heterocycloalkyl and heteroaryl. The term "substituted heterocyclic", as used herein, refers to substituted heterocycloalkyl and substituted heteroaryl.

The term "$C_1$–$C_6$ alkoxy", as used herein, refers to a $C_1$–$C_6$ alkyl group, as previously defined, attached to the parent molecular moiety through an oxygen atom. Examples of $C_1$–$C_6$-alkoxy include, but are not limited to, methoxy, ethoxy, propoxy, isopropoxy, n-butoxy, tert-butoxy, neopentoxy and n-hexoxy.

The term "$C_1$–$C_3$-alkylamino", as used herein, refers to one or two $C_1$–$C_3$-alkyl groups, as previously defined, attached to the parent molecular moiety through a nitrogen atom. Examples of $C_1$–$C_3$-alkylamino include, but are not limited to, methylamino, dimethylamino, ethylamino, diethylamino, and propylamino.

The term "alkylamino" refers to a group having the structure —NH($C_1$–$C_{12}$ alkyl) where $C_1$–$C_{12}$ alkyl is as previously defined.

The term "dialkylamino" refers to a group having the structure —N($C_1$–$C_{12}$ alkyl) ($C_1$–$C_{12}$ alkyl), where $C_1$–$C_{12}$ alkyl is as previously defined. Examples of dialkylamino are, but not limited to, dimethylamino, diethylamino, methylethylamino, piperidino, and the like.

The term "alkoxycarbonyl" represents an ester group, i.e. an alkoxy group, attached to the parent molecular moiety through a carbonyl group such as methoxycarbonyl, ethoxycarbonyl, and the like.

The term "carboxaldehyde", as used herein, refers to a group of formula —CHO.

The term "carboxy", as used herein, refers to a group of formula —COOH.

The term "carboxamide", as used herein, refers to a group of formula —C(O)NH($C_1$–$C_{12}$ alkyl) or —C(O)N($C_1$–$C_{12}$ alkyl)($C_1$–$C_{12}$ alkyl).

"Hydroxy protecting group", as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf, for example, T. H. Greene and P. G. M. Wuts, *Protective Groups in Organic Synthesis*, 3rd edition, John Wiley & Sons, New York (1999). Examples of hydroxy protecting groups include, but are not limited to, methylthiomethyl, tert-dimethylsilyl, tert-butyldiphenylsilyl, acyl substituted with an aromatic group and the like.

The term "protected hydroxy" refers to a hydroxy group protected with a hydroxy protecting group, as defined above, including benzoyl, acetyl, trimethylsilyl, triethylsilyl, methoxymethyl groups, for example.

"Aldehyde-protecting group", as used herein, refers to an easily removable group which is known to protect an aldehyde group against undesirable reaction during synthetic procedures and to be selectively removable. The use of aldehyde-protecting groups is well known in the art for protecting aldehyde groups against undesirable reactions during a synthetic procedure and many such protecting groups are known. See, for example, T. H. Greene and P. G. M. Wuts, *Protective Groups in Organic Synthesis*, op. cit. Examples of aldehyde-protecting groups include, but are not limited to, acetals, ketals, O-substituted cyanohydrins, substituted hydrazones, imines and the like.

The term "protected aldehyde", as used herein, refers to an aldehyde group protected with an aldehyde-protecting group, as defined above, including dimethyl acetyl, 1,3-dioxolane, 1,3-dioxane an the like.

"Amino-protecting group", as used herein, refers to an easily removable group which is known in the art to protect an amino group against undesirable reaction during synthetic procedures and to be selectively removable. The use of amino-protecting groups is well known in the art for protecting groups against undesirable reactions during a synthetic procedure and many such protecting groups are known, cf, for example, T. H. Greene and P. G. M. Wuts, *Protective Groups in Organic Synthesis*, op. cit. Examples of amino protecting groups include, but are not limited to, 9-fluorenylmethyl carbamate, benzyl carbonate, tert-butyl carbonate, benzyl, p-toluene sulfonyl, acyl and the like.

The term "protected amino", as used herein, refers to an amino group protected by an amino-protecting group, as defined herein.

The term "aprotic solvent", as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

The term "protogenic organic solvent", as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present. Further, in those cases where a bond between carbon atoms of the macrolide is a double bond both the cis and trans forms are within the scope of the invention described in this application.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolatior and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs", as used herein, refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. The term "prodrug" refers to compounds that are rapidly transformed in vivo to yield the parent compound of the above formula, for example by hydrolysis in blood. A thorough discussion is provided in T. Higuchi and V. Stella, "Pro-drugs as Novel Delivery Systems, Vol. 14 of the ACS Symposium Series, and in Edward B. Roche, ed., "Bioreversible Carriers in Drug Design", American Pharmaceutical Association and Pergamon Press, 1987, both of which are incorporated herein by reference.

Antibacterial Activity.

Susceptibility tests can be used to quantitatively measure the in vitro activity of an antimicrobial agent against a given bacterial isolate. Compounds were tested for in vitro antibacterial activity by a micro-dilution method. Minimal Inhibitory Concentration (MIC) was determined in 96 well microtiter plates utilizing the appropriate Mueller Hinton Broth medium (CAMHB) for the observed bacterial isolates. Antimicrobial agents were serially diluted (2-fold) in DMSO to produce a concentration range from about 64 $\mu$g/ml to about 0.03 $\mu$g/ml. The diluted compounds (2 $\mu$l/well) were then spotted to sterile 96-well microtiter plates. The inoculum for each bacterial strain was adjusted to 5.5×10$^5$ CFU/ml in appropriate MIC medium; 200 ul/well of this inoculum was added to the 96-well microtiter plate resulting in a final concentration of 1×10$^5$ CFU/ml. The 96 well plates were covered and incubated in a humidified atmosphere at 35+/−2° C. for 16–24 hours depending on the bacterial strain tested. Following incubation, plate wells were visually examined by Optical Density measurement for the presence of growth (turbidity). The lowest concentration of an antimicrobial agent at which no visible growth occurs was defined as the MIC. The compounds of the invention generally demonstrated an MIC in the range from about 64 µg/ml to about 0.03 µg/ml.

All in vitro testing follows the guidelines described in the Approved Standards M7-A5 protocol, published by the National Committee for Clinical Laboratory Standards (NCCLS).

Pharmaceutical Compositions.

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethyl cellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or other animal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other animal in single or in divided doses can be in amounts, for example, from 0.01 to about 50 mg/kg body weight or more usually from 0.1 to about 25 mg/kg body weight. Single dose compositions may contain such amounts or submultiples thereof to make up the daily dose. In general, treatment regimens according to the present invention comprise administration to a patient in need of such treatment of from about 10 mg to about 1000 mg of the compound(s) of this invention per day in single or multiple doses.

The pharmaceutical compositions of this invention can be administered to fish by blending them in the fish feed to be administered orally or may be dissolved in water in which sick fish are placed to swim around (a method using a so-called "medicated bath"). The dosage for the treatment of fish differs depending upon the purpose of administration (prevention or cure of disease) and type, size and extent of infection of the fish to be treated. Generally, a dosage of 5–1000 mg, preferably 20–100 mg, per kg of body weight of fish may be administered per day, either at one time or divided into several times. It will be recognized that the above-specified dosage is only a general range which may be reduced or increased depending on the age, body weight, condition of disease, etc. of the fish.

Abbreviations

Abbreviations which may be used in the descriptions of the schemes and the examples that follow are: Ac for acetyl; AIBN for 2,2-azobisisobutyronitrile; Bn for benzyl; Boc for t-butoxycarbonyl; Bu$_3$SnH for tributyltin hydride; Bz for benzoyl; CDI for carbonyldiimidazole; DBU for 1,8-diazabicyclo[5.4.0]undec-7-ene; DCC for 1,3-dicyclohexylcarbodiimide; DEAD for diethylazodicarboxylate; DIC for 1,3-diisopropylcarbodiimide; DIEA for diisopropylethylamine; DMAP for dimethylaminopyridine; DMF for dimethyl formamide; DMSO for dimethylsulfoxide; DPPA for diphenylphosphoryl azide; EtOAc for ethyl acetate; KHMDS for potassium bis (trimethylsilyl) amide; LDA for lithium diisopropyl amide; MeOH for methanol; Me$_2$S for dimethyl sulfide; MOM for methoxymethyl; OMs for mesylate; OTos for tosylate; NaN(TMS)$_2$ for sodium bis(trimethylsilyl)amide; NCS for N-chlorosuccinimide; NMO for 4-methylmorpholine N-oxide; PCC for pyridinium chlorochromate; PDC for pyridinium dichromate; Ph for phenyl; TEA for triethylamine; THF for tetrahydrofuran; TPP or PPh$_3$ for triphenylphosphine; TBS for tert-butyl dimethylsilyl; and TMS for trimethylsilyl.

Synthetic Methods

The compounds and processes of the present invention will be better understood in connection with the following synthetic schemes which are illustrative of the methods by which the compounds of the invention may be prepared. The groups L, X, R$_1$, R$_2$, and Rp are as defined previously unless otherwise noted below.

Scheme 1

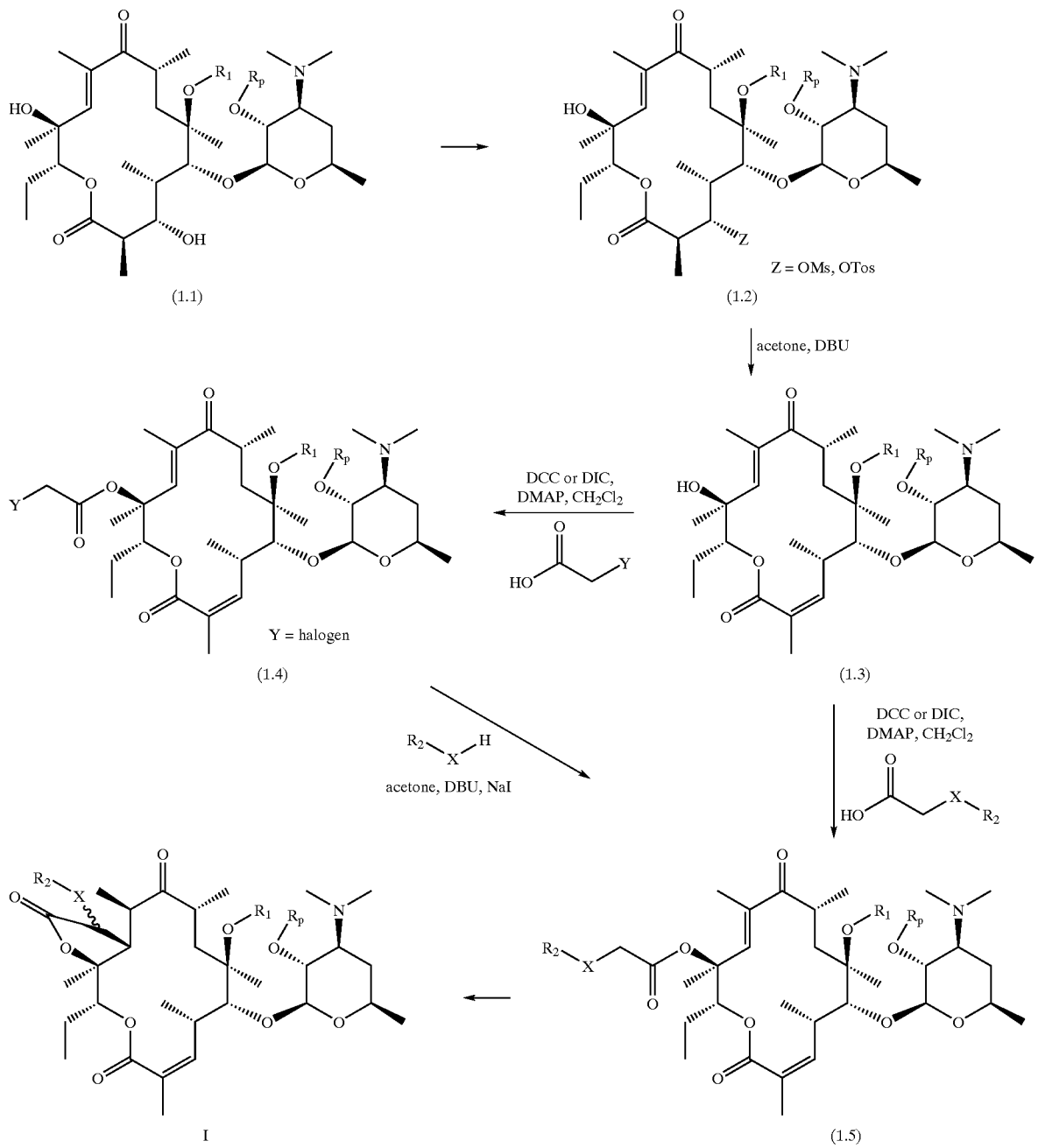

Scheme 1 illustrates the processes for the synthesis of compounds of formula I. The compounds of the present invention can be prepared by methods which are well known in the art by modification of the readily available compounds of formula (1.1) which can be prepared according to the processes described by Baker et al. *J. Org. Chem.* 1988, 53, 2340–2345; Elliott et al. *J. Med. Chem.* 1988, 41, 1651–1659; Ma et al. *J. Med. Chem.* 2001, 44, 4137–4156, and Or et al. U.S. Pat. No. 6,075,011-B1. Compounds of formula (1.1) are reacted with sulfonic anhydride, or sulfonyl chloride in an aprotic organic solvent such as methylene chloride, ethylene chloride, THF, chloroform or the like at a temperature from about −78° C. to about 50° C. for about 30 minutes to 48 hours in the presence of an amine base, such as pyridine, diethylamine, triethylamine or the like, optionally by adding a catalyst such as DMAP, imidazole or the like to provide compounds of formula (1.2) where Z is a mesylate or a tosylate. Compounds of formula (1.3) are obtained by treating compounds of formula (1.2) with a base such as DBU, DIEA, triethylamine or the like in solvents such as acetone, DMF, DMSO at a temperature from 25° C. to 100° C. for about 1 hour to 48 hours. Compounds of formula (1.3) are reacted with an acylating reagent to provide compounds of formulas (1.4) and (1.5). Typical acylating conditions include reacting compounds of formula (1.3) with an acid anhydride, a mixed anhydride, an acid halide, a carboxylic acid and the like, optionally in the presence of a catalyst such as DMAP, optionally in the presence of a dehydration reagent such as DCC, DIC or the like, and optionally in the presence of a base such as sodium hydride, potassium tert-butoxide, LDA, KHMDS or the like, in an aprotic solvent such as dichloromethane, chloroform, tetrahydrofuran, N-methylpyrrolidinone, dimethylsulfoxide, N,N-dimethylformamide, N,N-dimethylacetamide, hexamethylphosphoric triamide or the like or a mixture thereof at a temperature from −20° C. to 50° C. for 2–48 hours. A preferred acylating condition is reacting compounds of formula (1.3) with a carboxylic acid, DIC, and DMAP in dichloromethane at from 0° C. to room temperature. Compounds of formula (1.4), where Y is halogen or another activating group such as mesylate, tosylate or the like, can be converted to compounds of formula (1.5) by reacting with the anion of $R_2$—X—M where $R_2$ and X are previously defined and M is sodium, potassium, lithium or the like, or $R_2$—X—H in the presence of a base such as sodium hydride, potassium carbonate, LDA, sodium carbonate, DBU or the like in the presence of an aprotic solvent such as tetrahydrofuran, N-methylpyrrolidinone, dimethylsulfoxide, N,N-dimethylformamide, N,N-dimethylacetamide, hexamethylphosphoric triamide or the like, or a mixture thereof, at a temperature from −20° C. to 50° C. for 1–48 hours. Compounds of formula (1.5) undergo an intramolecular cyclization to provide compounds of formula (I) upon treatment with a base such as sodium hydride, potassium tert-butoxide, LDA, KHMDS or the like in an aprotic solvent such as tetrahydrofuran, N-methylpyrrolidinone, dimethylsulfoxide, N,N-dimethylformamide or the like, or a mixture thereof, at a temperature from −20° C. to 50° C. for 1–24 hours. The Rp protecting group of the compounds of formula (I) can be removed upon treatment with methanol at from room temperature to 50° C. for 2–48 hours.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Compound of Formula (I): L=$CH_2CH_3$, X=S, $R_1$=$CH_3$, $R_2$=2-[6-(Dimethylamino-methyleneamino) purin-9-yl]-ethyl and Rp=H Step 1a. Compound of Formula (1.1) of Scheme 1: $R_1$=$CH_3$ and Rp=Bz A solution of a compound of formula (1.1) of Scheme 1, where $R_1$ is $CH_3$ and Rp is H, (35.50 g, 62.17 mmol) and benzoyl anhydride (90%, 15.47 g, 68.39 mmol) in methylene chloride (300 mL) was heated to reflux overnight. The reaction mixture was diluted with additional methylene chloride (500 mL) and washed with a saturated aqueous solution of $NaHCO_3$, then with water and brine. The organic layers were dried over $Na_2SO_4$ and concentrated under reduced pressure to give the crude title compound (41.10 g, 98%).

MS (ESI) m/z 676 (M+H)$^+$; $^{13}$C-NMR (100 MHz, CDCl$_3$): δ 207, 175.5, 165.6, 162.3, 140.8, 139.3, 134.5, 132.7, 131.5, 129.8, 128.7, 102.8, 80.0, 79.2, 76.6, 73.2, 72.7, 72.1, 69.2, 64.0, 48.8, 44.0, 40.5, 37.7, 37.4, 37.0, 30.8, 21.1, 20.5, 20.3, 17.0, 14.4, 13.4, 10.4, 8.0.

Step 1b. Compound of Formula (1.2) of Scheme 1: $R_1$=$CH_3$, Rp=Bz and Z=OMs

Into a solution of the compound from Step 1a (5 g, 7.4 mmol) in pyridine (7 mL), was added methanesulfonic anhydride (Ms$_2$O) (1.55 g, 8.88 mmol) at room temperature. The reaction mixture was stirred at room temperature overnight. Additional Ms$_2$O (3.0 g, 17.6 mmol) was added. The mixture was stirred at room temperature for two days and at 45° C. for 6 hours. The mixture was treated with saturated NaHCO$_3$ aqueous solution and extracted with ethyl acetate. The organic layer was washed with saturated NaHCO$_3$ aqueous solution and with brine, then dried (Na$_2$SO$_4$), filtered and concentrated under reduced pressure. The crude residue was purified by flash chromatography (acetone:hexane, 3:7) to give 3.8 g of the title compound.

MS (ESI) m/z 754 (M+H)$^+$; $^{13}$C-NMR (125 MHz, CDCl$_3$): δ 206.8, 173.0, 165.2, 141.0, 132.5, 130.7, 129.7, 128.1, 122.9, 100.3, 87.1, 80.1, 78.4, 72.9, 72.1, 68.6, 63.4, 50.2, 43.6, 40.8, 40.7, 39.2, 38.9, 31.6, 31.5, 22.6, 21.9, 21.7, 21.2, 20.9, 16.3, 14.0, 13.6, 10.6.

Step 1c. Compound of Formula (1.3) of Scheme 1: $R_1$=$CH_3$ and Rp=Bz

Into a solution of the compound from Step 1b (3.5 g, 4.64 mmol) in acetone (50 mL), was added DBU (1.4 mL, 9.28 mmol) at room temperature. The reaction mixture was stirred at 50° C. overnight then at room temperature for one day. The mixture was taken up in ethyl acetate, washed with saturated NaHCO$_3$ aqueous solution and with brine, then dried (Na$_2$SO$_4$), filtered and concentrated under reduced pressure to give 3.5 g of the crude title compound.

MS (ESI) m/z 658 (M+H)$^+$.

Step 1d. Compound of Formula (1.4) of Scheme 1: $R_1$=$CH_3$, Rp=Bz and Y=Cl

Into a solution of the crude compound from Step 1c (1 g, 1.52 mmol) in dichloromethane (35 mL), chloroacetic acid (430 mg, 4.56 mmol) and DMAP (370 mg, 3.04 mmol) were added at room temperature. Into the reaction mixture a solution of DIC (714 μL, 4.56 mmol) in dichloromethane (5 mL) was added slowly over 15 minutes. The reaction mixture was stirred at room temperature overnight. Additional chloroacetic acid (288 mg, 3.04 mmol) and DIC (480 uL, 3.04 mmol) were added. The solid precipitate was removed by filtration and the filtrate treated with saturated NaHCO$_3$ aqueous solution and extracted with ethyl acetate. The extract was washed with saturated NaHCO$_3$ aqueous solution and with brine, then dried (Na$_2$SO$_4$), filtered and concentrated under reduced pressure. The crude residue was purified by flash chromatography (acetone:hexane, 1:4) to give the title compound (300 mg).

MS (ESI) m/z 734 (M+H)$^+$; $^{13}$C-NMR (125 MHz, CDCl$_3$): δ 206.8, 169.3, 165.4, 164.8, 145.7, 138.5, 135.7, 132.8, 130.5, 129.6, 128.2, 124.6, 102.2, 84.8, 84.6, 79.5, 77.5, 72.0, 69.3, 63.4, 49.9, 42.1, 40.8, 39.4, 37.3, 31.7, 31.5, 23.4, 22.9, 22.6, 21.0, 20.6, 19.5, 18.6, 13.9, 11.6, 10.5.

Step 1e. Compound of Formula (1.5) of Scheme 1: X=S, $R_1$=$CH_3$, $R_2$=2-(6-amino-purin-yl)-ethyl and Rp=Bz Into a solution of the compound from Step 1d (300 mg, 0.409 mmol) in acetone (3 mL), were added NaI (5 mg) and [6-amino-9H-purine]-1-ethanethiol (234 mg, (100 mg, 0.49 mmol) at room temperature. Into the resulting suspension, DBU (80 uL, 0.49 mmol) was added. The reaction mixture was stirred at room temperature for 3 hours and treated with NaHCO$_3$ aqueous solution. The resulting mixture was extracted with ethyl acetate. The organic layer was washed with saturated NaHCO$_3$ aqueous solution then with brine, and dried (Na$_2$SO$_4$), filtered and concentrated under reduced pressure. The crude residue was purified by flash chromatography (dichloromethane:2M NH$_3$ in methanol/98:2) to give the title compound (250 mg).

MS (ESI) m/z 893 (M+H)$^+$; $^{13}$C-NMR (125 MHz, CDCl$_3$): δ 207.2, 169.4, 167.8, 165.4, 155.4, 152.9, 150.0, 145.6, 140.9, 138.5, 135.6, 132.8, 130.5, 129.6, 128.2, 124.8, 119.6, 102.0, 84.5, 84.2, 79.5, 77.6, 72.0, 69.3, 63.4, 50.0, 42.9, 40.8, 39.5, 37.3, 34.1, 32.5, 31.7, 31.6, 22.9, 22.6, 21.0, 20.7, 19.5, 18.7, 14.1, 11.6, 10.6.

Step 1f. Compound of Formula (I): L=CH$_2$CH$_3$, X=S, R$_1$=CH$_3$, R$_2$=2-[6-(dimethylamino-methyleneamino)purin-9-yl]-ethyl and Rp=Bz Into a solution of the compound from Step 1e (30 mg, 0.033 mmol) in DMSO (0.8 mL) and THF(0.4 mL), was added potassium tert-butoxide (50 uL 1.0 M solution in THF, 0.05 mmol) at 0° C. dropwise. The reaction mixture was stirred at 0° C. for 1 hour, then treated with saturated NaHCO$_3$ aqueous solution. The resulting mixture was extracted with ethyl acetate. The organic layer was washed with saturated NaHCO$_3$ aqueous solution and with brine, then dried (Na$_2$SO$_4$), filtered and concentrated under reduced pressure to give the title compound as a crude mixture (24 mg).

MS (ESI) m/z 893 (M+H)$^+$.

Step 1g. Compound of Formula (I): L=CH$_2$C$_3$, X=S, R$_1$=CH$_3$, R$_2$=2-[6-(Dimethylamino-methyleneamino)purin-9-yl]-ethyl and Rp=H A solution of the crude compound from Step 1f (24 mg) in methanol (2 mL) was heated to reflux overnight, cooled to room temperature and concentrated under reduced pressure. The crude residue was purified by C$_{18}$ HPLC to give the title compound (2 mg).

MS (ESI) m/z 789 (M+H)$^+$; $^{13}$C-NMR (125 MHz, CDCl$_3$): δ 216.9, 176.0, 169.0, 155.0, 152.7, 149.9, 146.0, 142.4, 123.3, 119.8, 104.9, 88.3, 83.4, 79.6, 78.4, 70.3, 69.6, 65.9, 49.2, 47.8, 45.1, 41.9, 40.3, 38.8, 37.1, 35.8, 32.4, 29.7, 28.5, 22.3, 21.3, 20.7, 18.0, 17.0, 15.4, 15.3, 13.0, 10.9.

Example 2

Compound of Formula (I): L=CH$_2$CH$_3$, X=S, R$_1$=CH$_3$, R$_2$=3-(3-Pyridinyl)-1H-pyrazole-ethyl and Rp=H Step 2a. Compound of Formula (1.5) of Scheme 1: X=S, R$_1$=CH$_3$, R$_2$=3-(3-Pyridinyl)-1H-pyrazole-ethyl Rp=Bz The title compound is obtained according to the procedure described in Step 1e of Example 1 from the compound of Step 1d and [3-(3-pyridinyl)-1H-pyrazole]-1-ethanethiol (prepared as described in WO200216380-A1).

Step 2b. Compound of Formula (I): L=CH$_2$CH$_3$, X=S, R$_1$=CH$_3$, R$_2$=3-(3-Pyridinyl)-1H-pyrazole-ethyl and Rp=Bz The title compound is obtained from the compound of Step 2a according to the procedure described in Step 1f of Example 1.

Step 2c. Compound of Formula (I): L=CH$_2$CH$_3$, X=S, R$_1$=CH$_3$, R$_2$=3-(3-Pyridinyl)-1H-pyrazole-ethyl and Rp=H The title compound is obtained from the compound of Step 2b according to the procedure described in Step 1g of Example 1.

Example 3

Compound of Formula (I): L=CH$_2$CH$_3$, X=S, R$_1$=CH$_3$, R$_2$=[3-(3-Pyridinyl)-1H-1,2,4-triazole-1-yl]-ethyl and Rp=H Step 3a. Compound of Formula (1.5) of Scheme 1: X=S, R$_1$=CH$_3$, R$_2$=[3-(3-Pyridinyl)-1H-1,2,4-triazole-1-yl]-ethyl and Rp=Bz The title compound is obtained from the compound of Step 1d of Example 1 and [3-(3-pyridinyl)-1H-1,2,4-triazole-1-yl]-ethanethiol (prepared as described in WO200216380-A1) according to the procedure described in Step 1e.

Step 3b. Compound of Formula (I): L=CH$_2$CH$_3$, X=S, R$_1$=CH$_3$, R$_2$=[3-(3-Pyridinyl)-1H-1,2,4-triazole-1-yl]-ethyl and Rp=Bz The title compound is obtained from the compound of Step 3a according to the procedure described in Step 1f of Example 1.

Step 3c. Compound of Formula (1): L=CH$_2$CH$_3$, X=S, R$_1$=CH$_3$, R$_2$=[3-(3-Pyridinyl)-1H-1,2,4-triazole-1-yl]-ethyl and Rp=H The title compound is obtained from the compound of Step 3b according to the procedure described in Step 1g of Example 1.

Example 4

Compound of Formula (1): L=CH$_2$CH$_3$, X=S, R$_1$=CH$_3$, R$_2$=[4-(3-Pyridinyl)-1H-imidazole]-1-ethyl and Rp=H Step 4a. Compound of Formula (1.5) of Scheme 1: X=S, R$_1$=CH$_3$, R$_2$=[4-(3-Pyridinyl)-1H-imidazole]-1-ethyl and Rp=Bz The title compound is obtained from the compound of Step 1d of Example 1 and [4-(3-pyridinyl)-1H-imidazole]-1-ethanethiol (prepared as described in WO200216380-A1) according to the proedure described in Step 1e of Example 1.

Step 4b. Compound of Formula (I): L=CH$_2$CH$_3$, X=S, R$_1$=CH$_3$, R$_2$=[4-(3-Pyridinyl)-1H-imidazole]-1-ethyl and Rp=Bz The title compound is obtained from the compound of Step 4a according to the procedure described in Step 1f of Example 1.

Step 4c. Compound of Formula (1): L=CH$_2$CH$_3$, X=S, CH$_3$, R$_2$=[4-(3-Pyridinyl)-1H-imidazole]-1-ethyl and Rp=H The title compound is obtained from the compound of Step 4b according to the procedure described in Step 1g of Example 1.

Although the invention has been described in detail with respect to various preferred embodiments it is not intended to be limited thereto, but rather those skilled in the art will recognize that variations and modifications may be made therein which are within the spirit of the invention and the scope of the appended claims.

What is claimed is:

1. A compound represented by the formula

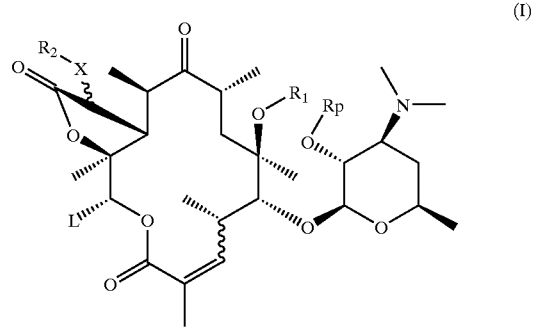

(I)

and the pharmaceutically acceptable salts, esters and prodrugs thereof, wherein

L is selected from the group consisting of:
(1) —CH(OH)CH$_3$;
(2) C$_1$–C$_6$ alkyl, optionally substituted with one or more substituents selected from the group consisting of aryl, substituted aryl, heteroaryl and substituted heteroaryl;
(3) C$_2$–C$_6$ alkenyl, optionally substituted with one or more substituents selected from the group consisting of aryl, substituted aryl, heteroaryl and substituted heteroaryl; and
(4) C$_2$–C$_6$ alkynyl, optionally substituted with one or more substituents selected from the group consisting of aryl, substituted aryl, heteroaryl and substituted heteroaryl;

R$_1$ is selected from the group consisting of C$_1$–C$_6$-alkyl, C$_2$–C$_6$-alkenyl and C$_2$–C$_6$-alkynyl, each optionally substituted with one or more substituents selected from the group consisting of:
(1) halogen;
(2) aryl;
(3) substituted aryl;
(4) heteroaryl;
(5) substituted heteroaryl;
(6) —O—R$_5$, where R$_5$ is selected from the group consisting of:
  a. hydrogen;
  b. aryl;
  c. substituted aryl;
  d. heteroaryl; and
  e. substituted heteroaryl;
(7) —O—C$_1$–C$_6$-alkyl-R$_5$;
(8) —O—C$_2$–C$_6$-alkenyl-R$_5$;
(9) —O—C$_2$–C$_6$-alkynyl-R$_5$; and
(10) —NR$_6$R$_7$, where R$_6$ and R$_7$ are each independently selected from the group consisting of: hydrogen; C$_1$–C$_6$-alkyl, optionally substituted with one or more substituents selected from the group consisting of halogen, aryl, substituted aryl, heterocyclic and substituted heterocyclic; C$_2$–C$_6$-alkenyl, optionally substituted with one or more substituents selected from the group consisting of halogen, aryl, substituted aryl, heterocyclic and substituted heterocyclic; and C$_2$–C$_6$-alkynyl, optionally substituted with one or more substituents selected from the group consisting of halogen, aryl, substituted aryl, heterocyclic and substituted heterocyclic; or R$_6$R$_7$ taken together with the nitrogen atom to which they are connected form a 3- to 7-membered ring which may optionally contain one or more hetero functions selected from the group consisting of —O—, —NH—, —N(C$_1$–C$_6$-alkyl)-, —N(aryl)-, —N(heteroaryl)-, —S—, —S(O)— and —S(O)$_2$—;

R$_2$ is selected from the group consisting of:
(1) hydrogen;
(2) C$_1$–C$_6$-alkyl, optionally substituted with one or more substituents selected from the group consisting of:
  a. halogen;
  b. aryl;
  c. substituted aryl;
  d. heterocyclic;
  e. substituted heterocyclic;
  f. —O—R$_3$, where R$_3$ is selected from the group consisting of:
    i. hydrogen;
    ii. aryl;
    iii. substituted aryl;
    iv. heteroaryl; and
    v. substituted heteroaryl;
  g. —O—C$_1$–C$_6$-alkyl-R$_3$;
  h. —O—C$_2$–C$_6$-alkenyl-R$_3$;
  i. —O—C$_2$–C$_6$-alkynyl-R$_3$; and
  j. —NR$_6$R$_7$;
(3) C$_2$–C$_6$-alkenyl, optionally substituted with one or more substituents selected from the group consisting of:
  a. halogen;
  b. aryl;
  c. substituted aryl;
  d. heterocyclic;
  e. substituted heterocyclic;
  f. —O—R$_3$;
  g. —O—C$_1$–C$_6$-alkyl-R$_3$;
  h. —O—C$_2$–C$_6$-alkenyl-R$_3$;
  i. —O—C$_2$–C$_6$-alkynyl-R$_3$; and
  j. —NR$_6$R$_7$; and
(4) C$_2$–C$_6$-alkynyl, optionally substituted with one or more substituents selected from the group consisting of:
  a. halogen;
  b. aryl;
  c. substituted aryl;
  d. heterocyclic;
  e. substituted heterocyclic;
  f. —O—R$_3$;
  g. —O—C$_1$–C$_6$-alkyl-R$_3$;
  h. —O—C$_2$–C$_6$-alkenyl-R$_3$;
  i. —O—C$_2$–C$_6$-alkynyl-R$_3$; and
  j. —NR$_6$R$_7$;

X is selected from the group consisting of:
(a) S(O)n, where n is 0, 1, or 2;
(b) O; and
(c) NR$_5$; and Rp is hydrogen or a hydroxy protecting group.

2. A compound according to claim 1 wherein L is CH$_2$CH$_3$, X is —S—, R$_1$ is CH$_3$ and R$_2$ and Rp are as defined in claim 1.

3. A compound according to claim 1 which is selected from the group consisting of:
Compound of formula (I): L=CH$_2$CH$_3$, X=S, R$_1$=CH$_3$, R$_2$=2-[6-(dimethylamino-methyleneamino)purin-9-yl]-ethyl and Rp=H;
Compound of formula (I): L=CH$_2$CH$_3$, X=S, R$_1$=CH$_3$, R$_2$=2-(6-amino-purin-yl)-ethyl and Rp=H;
Compound of formula (I): L=CH$_2$CH$_3$, X=S, R$_1$=CH$_3$, R$_2$=3-(3-pyridinyl)-1H-pyrazole-ethyl and Rp=H;
Compound of formula (I): L=CH$_2$CH$_3$, X=S, R$_1$=CH$_3$, R$_2$=[3-(3-pyridinyl)-1H-1,2,4-triazole-1-yl]-ethyl and Rp=H;
Compound of formula (I): L=CH$_2$CH$_3$, X=S, R$_1$=CH$_3$, R$_2$=[4-(3-pyridinyl)-1H-imidazole]-1-ethyl and Rp=H; and
Compound of formula (I): L=CH$_2$CH$_3$, X=O, R$_1$=CH$_3$, R$_2$=CH$_2$CH$_2$-phenyl and Rp=H.

4. A pharmaceutical composition comprising a therapeutically effective amount of a compound of claim 1, or a pharmaceutically-acceptable salt, ester or prodrug thereof, in combination with a pharmaceutically acceptable carrier.

5. A method for controlling a bacterial infection in an animal comprising administering to an animal a therapeutically-effective amount of a pharmaceutical composition according to claim 4.

6. A process for preparing a compound represented by the formula

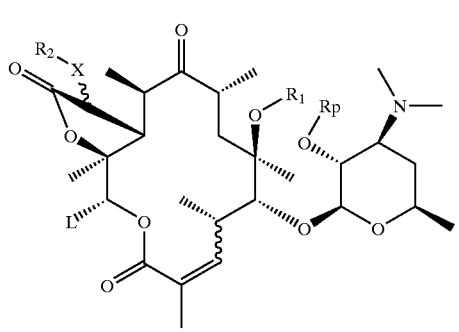

(I)

wherein L, X, $R_1$, $R_2$, and Rp are as defined in claim 1, the method comprising (a) acylating a compound represented by the formula

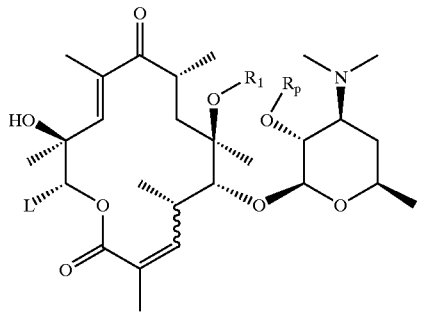

wherein L and $R_1$ are as defined in claim 1 and Rp is a hydroxy protecting group, by reaction with a carboxylic acid, optionally in the presence of a catalyst, optionally in the presence of a dehydration reagent and optionally in the presence of a base in an aprotic organic solvent to provide a product represented by the formula

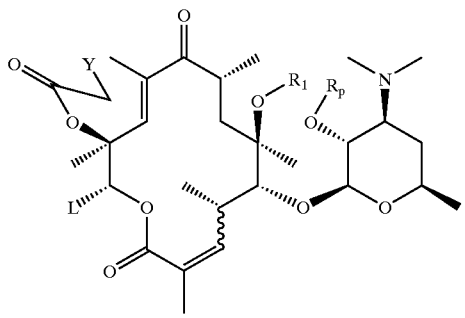

wherein L, $R_1$, and Rp are as defined in claim 1, and where Y is halogen;

(b) reacting a compound from step a with an anion of $R_2$—X—M where $R_2$ and X are as defined in claim 1, Rp is a hydroxy protecting group and M is sodium, potassium, or lithium, or $R_2$—X—H in the presence of a base in the presence of an aprotic solvent at a temperature from −20° C. to 50° C. for 1–48 hours to provide compound represented by the formula

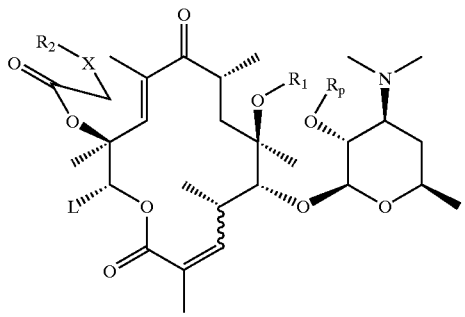

wherein L, $R_1$, $R_2$, Rp and X are as defined in claim 1; and
(c) reacting a compound from step b with a base in organic solvent to effect cyclization to provide a compound of formula (I).

* * * * *